United States Patent
Ohne et al.

[11] Patent Number: 6,024,569
[45] Date of Patent: Feb. 15, 2000

[54] ROOT CANAL FILLING POINT

[75] Inventors: Mitsuasa Ohne, Fukusima; Yasuo Yamazaki, Tokyo; Kazuo Shiiki, Fukusima, all of Japan

[73] Assignee: Aytec Japan Corporation, Tokyo, Japan

[21] Appl. No.: 09/187,928

[22] Filed: Nov. 6, 1998

[51] Int. Cl.[7] .................................. A61C 5/02
[52] U.S. Cl. ........................ 433/224; 433/228.1
[58] Field of Search ................. 433/81, 224, 228.1

[56] References Cited

U.S. PATENT DOCUMENTS

| | | | |
|---|---|---|---|
| 1,463,963 | 8/1923 | Miller | 433/224 |
| 1,757,595 | 5/1930 | Siegel | 433/224 |
| 3,925,895 | 12/1975 | Kliment et al. | 433/224 |
| 4,197,234 | 4/1980 | Temin | 260/42.27 |
| 4,304,766 | 12/1981 | Chang | 424/52 |
| 4,396,377 | 8/1983 | Roemer et al. | 433/199 |
| 4,552,906 | 11/1985 | Podszun et al. | 523/115 |
| 4,654,006 | 3/1987 | Kusano et al. | 433/168.1 |
| 4,758,612 | 7/1988 | Wilson et al. | 524/5 |
| 4,764,117 | 8/1988 | Yamashita et al. | 433/215 |
| 4,813,876 | 3/1989 | Wang | 433/224 |
| 5,071,499 | 12/1991 | Torres | 149/109.4 |
| 5,088,927 | 2/1992 | Lee | 433/224 |
| 5,113,880 | 5/1992 | Honda et al. | 132/321 |
| 5,141,560 | 8/1992 | Combe et al. | 433/228.1 |
| 5,185,386 | 2/1993 | Cohen | 523/105 |
| 5,276,068 | 1/1994 | Waknine | 552/28 |
| 5,444,104 | 8/1995 | Waknine | 522/24 |
| 5,728,768 | 3/1998 | Saxena et al. | 524/506 |
| 5,865,623 | 2/1999 | Suh | 433/228.1 |

*Primary Examiner*—Ralph A. Lewis
*Attorney, Agent, or Firm*—Kubovcik & Kubovcik

[57] ABSTRACT

A new root canal filling point which is physicochemically stable, is not toxic to periapical tissue, can be sterilized and x-rayed; and has high elasticity and fracture resistance which enables the root canal filling point to be pressure-inserted into an even narrow or curved root canal. The root canal filling point is made of a copolymer consisting of propylene and ethylene, and a contrast medium.

6 Claims, 4 Drawing Sheets

SEE FIG. 3A

ROOT CANAL FILLING POINT

BACKGROUND OF THE INVENTION (1) Field of the Invention

The present invention relates to a root canal filling point which is used to fill a root canal after pulpectomy (extirpation of the pulp). More particularly, the present invention relates to a new root canal filling point which is physicochemically stable, is not toxic to periapical tissue, can be sterilized easily and X-rayed; and has high elasticity and fracture resistance which enable this root canal filling point to be pressure-inserted into an even narrow or curved root canal.

(2) Description of the Prior Art

Dental caries that develops in enamel spreads to dentine and eventually reaches to the pulp, causing pulpitis. Pulpitis is treated by extirpating the infected pulp and filling root canal (see FIGS. 1 and 2).

Teeth are comprised of enamel (1), dentine (2), cement (3), root canals including pulp (4), and apical holes (5). Apical holes (5) are connected to the surrounding periapical tissue. A typical procedures for filling a root canal following pulpectomy are as follows: After infected pulp is removed, root canal is expanded using a reamer (6) and filled with a root canal filling point (7). The gap between the root canal filling point (7) and the root canal wall is filled by a root canal filling sealer (8), and the apical hole is closed.

Root canal filling point should have the following characteristics: (A) it can be easily sterilized, (B) it is not deleterious to the surrounding periapical tissue, (C) it can be easily inserted into narrow and curved root canals by pressure-filling, (D) it can tightly seal the root canal wall and apical holes, (E) it does not shrink or deteriorate after root canal filling, (F) it can be X-rayed, and (G) it can be removed when necessary (Grossman L. I.: Endodontic practice, 10th edition, p 279 LEA and FEBIGER Philadelphia, 1981).

Gutta-percha point, which is made of macromolecular polymers (consisting of isoprene monomer) and zinc, is commonly used to fill root canals. However, root canal filling point made of gutta-percha has the following disadvantages: 1) it cannot be sterilized by any methods other than gas sterilization, 2) due to it's low elasticity and fracture resistance, it cannot be easily pressure-inserted into narrow and curved root canals, 3) it tends to be weakened under normal usage conditions, and 4) it is subjected to phagocytosis in the body.

Silver point have also been utilized. However, because it is extremely difficult to remove it once it is inserted, the silver point is seldom used today.

Points made of such materials as acrylic, epoxy resin, nylon, teflon, polyvinyl, polypropylene, polyethylene, and silicone have been produced experimentally. Of these, points made of polypropylene or polyethylene showed some potential for clinical application, but when a filler was added to these points so that they could be X-rayed, their physicochemical properties were adversely affected. As a result, such points were never developed for clinical use. Incidentally, the type and contents of the fillers used for these points have not been reported in documents (Grossman L. I.: Trans. Third International. Conf. Endodont., Univ. Pennsylvania Press, Phila., p 125, 1963).

OBJECT AND SUMMARY OF THE INVENTION

The present invention was developed in an attempt to produce a root canal filling point which is easy-to-use, physicochemically stable; can be sterilized easily in an autoclave, can be X-rayed; and have low antigenicity, have appropriate elasticity and hardness so that they can be pressure-inserted into an even narrow and curved root canal; and are not deleterious to the surrounding periapical tissue. Furthermore, it should be made of non-degradable plastic so that it can remain in the body for a long time.

According to the present invention, there is provided a root canal filling point which is made of copolymer consisting mainly of propylene and ethylene, and contains a contrast medium.

DETAILED DESCRIPTION OF THE INVENTION

Figure 1:
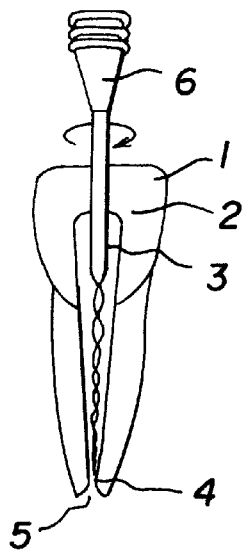
FIG. 1 shows pulpitis treatment.
Figure 2:
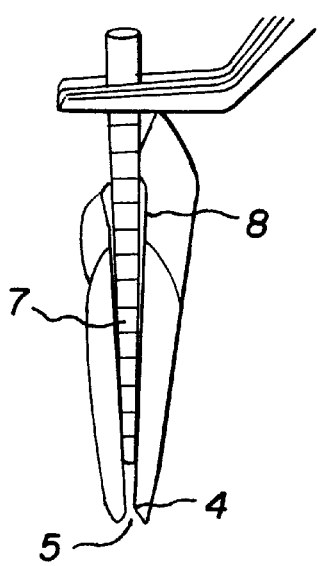
FIG. 2 shows root canal filling using a root canal filling point.

The proposed root canal filling point is made of copolymer consisting mainly of propylene and ethylene. Since the copolymer does not act as foreign object in the body, it will not be absorbed. Also, the copolymer is physically and physicochemically stable, and the components thereof does not dissolve. The copolymer is highly elastic, have high fracture resistance, and highly chemicals-, heat- and radiation-resistant during various sterilization processes. Accordingly, the copolymer has highly desirable characteristics for a root canal filling point.

The copolymer could be produced by, for example, a liquid-phase bulk polymerization method. More specifically, the copolymer could be produced by, for example, a method disclosed in Japanese Patent Publication Sho. 61-38925. That is, the method for producing a propylene-ethylene block copolymer in which polymerization of ethylene/propylene is carried out by a continuous system with a reaction ratio of 6/94% by weight or less for effecting a multi-step polymerization, with two or more tanks of polymerization tanks connected to each other by using a stereoregular catalyst and polymerization of ethylene/propylene with a reaction ratio of 15/85 to 95/5% by weight is carried out batch-wisely to give the propylene-ethylene block copolymer.

The stereoregular catalyst to be used in the above method is not particularly limited so long as it is a catalyst to be generally used for a stereoregular catalyst of propylene, and preferably a catalyst comprising (a) a solid catalyst containing at least three kinds of elements, Mg, Ti and Cl, and (b) an organic aluminum compound.

The solid catalyst containing at least three kinds of elements, Mg, Ti and Cl, can be obtained by various methods, for example, as proposed in Japanese Laid-Open Patent Application Sho. 54-103494, Japanese Laid-Open Patent Application Sho. 54-116079, Japanese Laid-Open Patent Application Sho. 55-102606, etc.

The organic aluminum compound (a solid catalyst) may be used in combination with a compound having at least one C—O or C—N bonding such as ester (e.g., methyl benzoate), ether (e.g., dibutyl ether), orthoester (e.g., methyl orthobenzoate), amine (e.g., triethyl amine) and the like.

The ratio of respective components to be used constituting the catalyst to be used in the above method is optional, and the suitable range is different depending on the compound to be used. However, in general, based on 1 mole of Ti in the solid catalyst, the organic aluminum compound is 0.1 to 500 moles, and the compound having at least one C—O or C—N bonding is in the range of 0 to 250 moles.

The mixing ratio of ethylene to propylene is not restricted, but preferably, in a range of 1.0–10.0% by weight, for example, 4% by weight. When ethylene is added to propylene in the ratio of 1.0–10.0% by weight to allow copolymerization to take place, the fluidity of the mixture during polymerization is such that it is possible to mold points accurately in accordance with the international specifications. The resultant copolymer possesses appropriate hardness and bending strength.

The contrast medium used in the present invention is at least one kind of particle, preferably super-fine particles having an average particle diameter of 1.0–8.0 $\mu$m, selected from the group consisting of barium sulfate ($BaSO_4$), zirconia ($ZrO_2$) and titania ($TiO_2$) particles. Of these, barium sulfate is the most suitable contrast medium.

The contrast medium contents is not restricted, and could be adjusted depending on the narrowness of the root canal filling point (the narrower the root canal filling point, the higher the contrast medium contents).

When barium sulfate ($BaSO_4$) is added to the copolymer in the amount of 40–70% by weight, the resultant compound can be X-rayed in accordance with ISO specifications (50% X-ray density). The barium sulfate content is also adjusted depending on the narrowness of root canal filling point. The narrowest root canal filling point (0.3 mm diameter) should ideally contain 70% of barium sulfate.

Root canal filling point according to the present invention can be produced by injection molding after dissolving copolymer and adding the contrast medium. Since the fluidity of the copolymer is appropriate for molding, root canal filling point can be made in accordance with the international specifications. The basic configuration of the root canal filling point conforms to the international specifications: the point is about 28 mm in length, with a circular cross section and a tapered tip. The diameter of root canal filling point according to the present invention ranges from 0.3 mm to 1.4 mm, and point is selected depending on the size of root canals.

Figure 3:
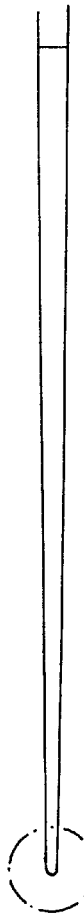
FIG. 3 shows basic configurations agreed with the international specifications, having circular cross-section and a tapered tip.
Figure 3A:
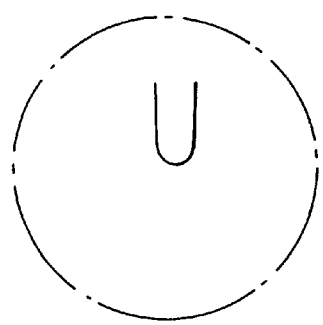
Figure 4:
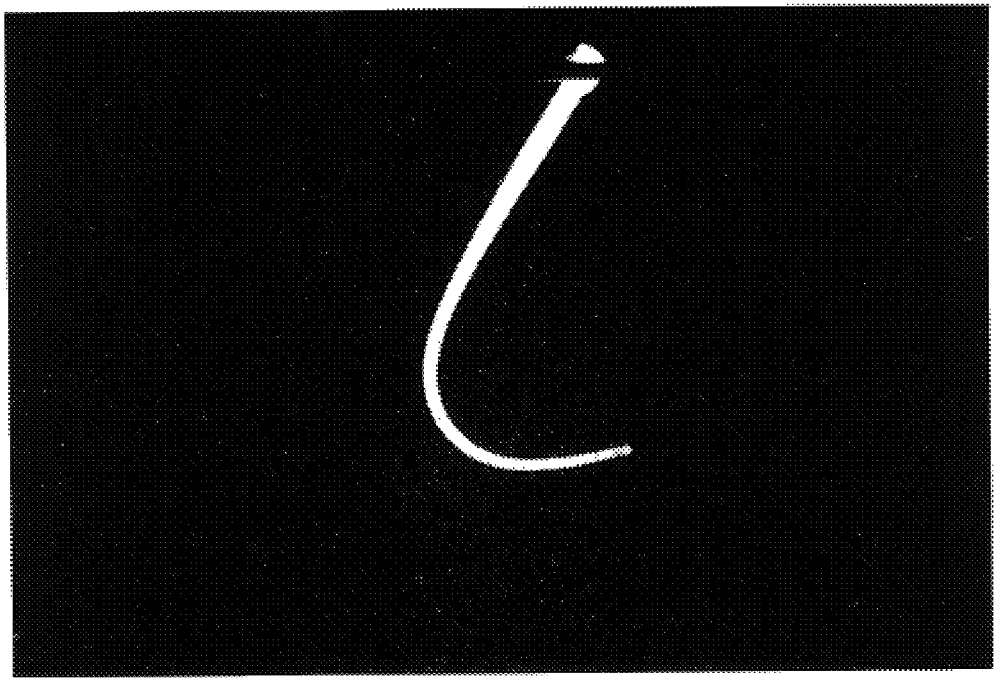
FIG. 4 shows an example of a root canal filling point according to the present invention which is bent at more than 90-degree angle.

FIG. 3 shows a magnified root canal filling point made of copolymer consisting mainly of propylene and ethylene with 70% barium sulfate (0.5 mm tip). Since this root canal filling point is highly elastic, and has appropriate hardness and high fracture resistance, it does not break when it is bent at more than 90-degree angle (see FIG. 4). Also, the point returned to its original shape.

Figure 5:
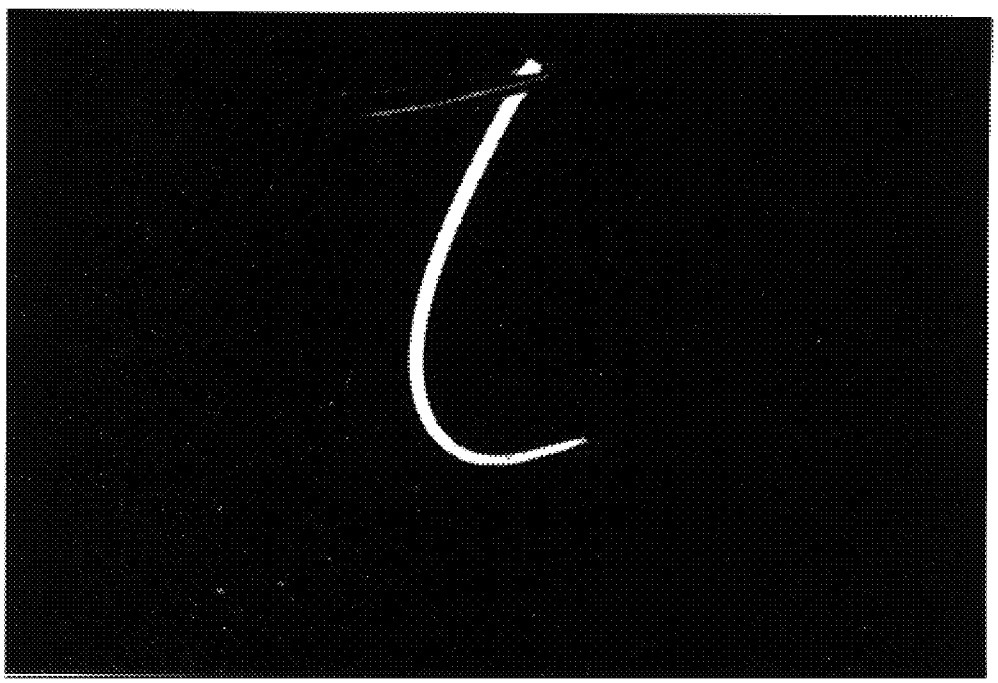
FIG. 5 shows a root canal filling point made of gutta-percha which is bent at more than 90-degree angle.

On the other hand, gutta-percha points were more likely to break when bent at a 90-degree angle, and even when they remained intact, they did not return to their original shape (see FIG. 5).

Figure 6:
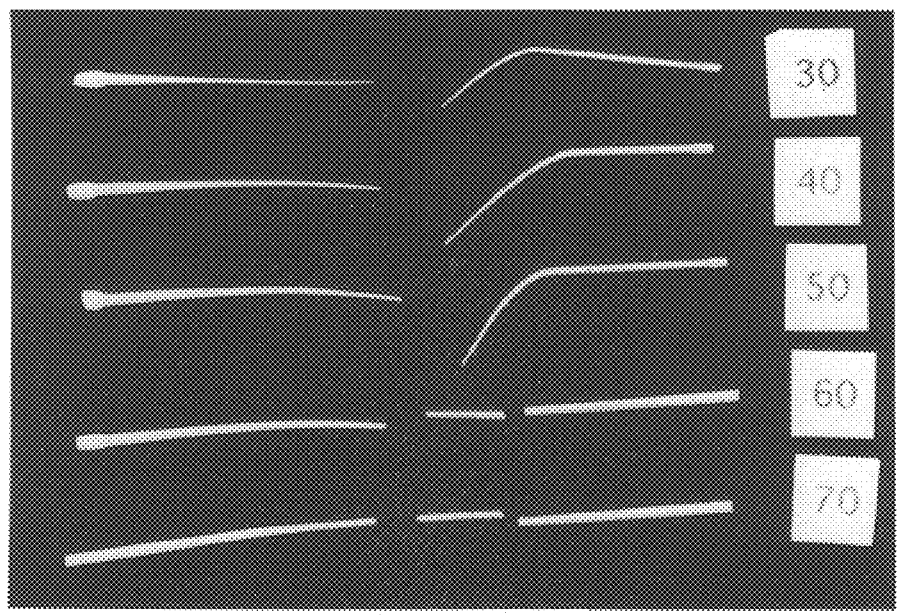
FIG. 6 shows root canal filling points having five different tip sizes according to the present invention (left group), and root canal filling point s made of gutta-percha, having five different tip sizes, after they are bent at more than 90-degree angle.

When root canal filling points made of the copolymer having five different tip sizes (ISO 30: 0.3 mm, ISO 40: 0.4 mm, ISO 50: 0.5 mm, ISO 60: 0.6 mm, and ISO 70: 0.7 mm) were bent at more than 90-degree angle, all of these points returned to their original shape. On the other hand, when gutta-percha points having five different tip sizes (ISO 30: 0.3 mm, ISO 40: 0.4 mm, ISO 50: 0.5 mm, ISO 60: 0.6 mm, and ISO 70: 0.7 mm) were bent at the same angle as above, ISO 30: 0.3 mm, ISO 40: 0.4 mm and ISO 50: 0.5 mm points did not return to their original shapes, and ISO 60: 0.6 mm and ISO 70: 0.7 mm points broke. The white points on the left are root canal filling points according to the present invention and those on the right are gutta-percha points (see FIG. 6).

The present invention is hereinafter described specifically by way of Examples and Comparative Examples.

EXAMPLES

Production of Copolymer

Copolymer consisting mainly of propylene and ethylene was produced according to Examples described in Japanese Patent Publication Sho. 61-38925. The method is characterized, in addition to a method for producing a propylene-ethylene block copolymer as mentioned above, in that an improvement is applied. In this method, the catalyst activity is lowered ¼ or less by adding a catalyst activity lowering agent to a slurry simultaneously with transferring the slurry to the polymerization tank at which a batch-wise reaction is carried out or before transferring the slurry than the activity of adding no said lowering agent, then the batch-wise polymerization is carried out under the conditions that the activity is heightened 1.1-folds or more by adding an organic aluminum compound to the slurry after completion of transfer thereof to the polymerization tank at which the batch-wise polymerization is carried out than the activity before said organic aluminum compound is added, and then the activity is lowered ½ or less by adding a catalyst activity lowering agent simultaneously with completion of the polymerization at the batch-wise polymerization tank than the activity before said lowering agent is added.

The number average molecular weight of the copolymer (block copolymer) consisting mainly of propylene and ethylene was about 200,000, the average polymerization degree was about 5,000, and the mixing ratio of ethylene to propylene was 4% by weight.

Production of Root Canal Filling Point

The root canal filling point according to the present invention was produced by an injection molding using the copolymer and contrast medium. The contrast medium is barium sulfate ($BaSO_4$) and was used 70% by weight.

EXAMPLE 1

Extirpated tooth

Figure 7:
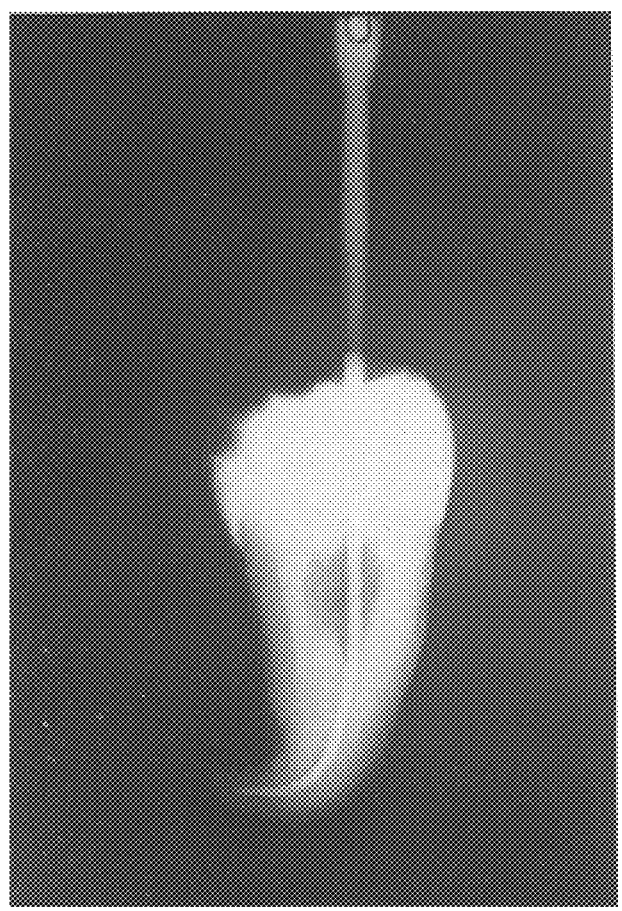
FIG. 7 shows an X-ray of an extirpated human tooth which was enlarged to accommodate a root canal filling point according to the present invention

Since the root canal filling point according to the present invention have high elasticity, hardness and fracture resistance, it can easily be inserted into the narrow or curved root canals of human teeth. FIG. 7 shows an X-ray of an extirpated human tooth whose root canal was enlarged to ISO 30 (0.3 mm) to accommodate an ISO 30 (0.3 mm) root canal filling point according to the present invention. The point was inserted into the enlarged area. The X-ray showed that the point was inserted satisfactorily. Its X-ray density, which was measured by an X-ray density analyzer, satisfied the ISO specifications for root canal filling point.

EXAMPLE 2

Clinical case

Figure 8:
FIG. 8 shows an X-ray of the root canals (one distal root and two proximal roots) of a human tooth which were enlarged after pulpectomy and the corresponding root canal filling points according to the present invention are inserted.

After pulpectomy, the root canals of a tooth were enlarged (one distal root was enlarged to ISO 70: 0.7 mm and two proximal roots to ISO 30: 0.3 mm), and the corresponding root canal filling points according to the present invention were inserted into the root canals with a sealer. As shown in FIG. 8, the root canals were tightly filled.

The advantages of root canal filling point according to the present invention over conventional root canal filling points (in particular, gutta-percha points) are as follows:

1) Conventional root canal filling point such as gutta-percha point is not elastic and is easily fractured, so it is difficult to insert into narrow or curved root canals. On the other hand, since root canal filling point according to the present invention is highly elastic and has fracture resistance, it can be easily inserted into even narrow or curved root canals. This is properly essential to ensure that root canal is filled accurately.

2) Root canal filling material must be removed if teeth require further treatment. Since conventional root canal filling point changes their shape over time, it is very difficult to remove from the teeth. On the other hand, since root canal filling point according to the present invention does not change their shape, it can be easily removed.

3) When conventional root canal filling point is sterilized by a method other than gas sterilization, it becomes unusable (due to melting or change in shape). On the other hand, root canal filling point according to the present invention can be sterilized thoroughly by all currently available sterilization methods without melting or change in shape or properties. This is extremely important, since root canal filling point is used as implants.

4) Conventional root canal filling point is subjected to phagocytosis, and therefore absorbed by the body. In other words, conventional point is recognized as foreign compounds by the human body. On the other hand, since the root canal filling point according to the present invention does not act as foreign matter in the human body, it is not subjected to phagocytosis. These characteristics suggest that root canal filling point according to the present invention can completely seal root canals and that it is unlikely to induce allergic reactions. The latter is a very important characteristic for biological materials.

5) Since conventional root canal filling point is to be weakened both inside and outside of the human body, its components can dissolve in the body. On the other hand, since copolymerization is completed before molding for root canal filling point according to the present invention, the point is very stable chemically in the body, and the monomers and contrast medium do not dissolve. Root canal filling point according to the present invention is therefore not deleterious to the periapical tissue or other parts of the body. This is a very important characteristic for biological materials.

6) In order to ascertain the extent of filling, it must be possible to observe root canal filling point by means of X-rays. The ISO specifications require an X-ray density of 50%. Conventional root canal filling point can be X-rayed when zinc or barium sulfate is added. However, as mentioned above, conventional root canal filling point is affected by phagocytosis, degradation, and alteration, which cause contrast media to dissolve. On the other hand, when root canal filling point according to the present invention is X-rayed in accordance with ISO specifications, since polymerization is completed, the contrast medium does not dissolve.

7) Since root canal filling point according to the present invention exhibits appropriate fluidity during molding, the configuration meets the international specifications. As a result, root canals can be filled accurately. The diameter of the tip of root canal filling point ranges from 0.3 mm to 1.4 mm, and the length is about 28 mm. An appropriate root canal filling point is selected depending on the size of root canals.

As mentioned above, root canal filling point can be made of either polymer polypropylene or polymer alone (homopolymer) polyethylene, but when a filler was added so that such points could be X-rayed with an X-ray density of about 50–60%, they became fragile. Consequently, such points were never developed for clinical use. The type and grain size of the filler were not recorded. The inventors of the present invention attempted to develop root canal filling point by using either polymer polypropylene or polymer polyethylene and adding various contrast media. However, the fluidity of these samples was poor, and contrast media could not be evenly distributed in root canal filling points during molding, which resulted in breakage.

In order to overcome the above problems, inventors employed copolymer consisting mainly of propylene and ethylene, and added 40–70% of contrast media such as barium sulfate. The X-ray density of the resultant point was 50%, which satisfied the ISO specifications, and the elasticity, hardness, and fracture resistance of the point was significantly improved. The reason for this was improvement that, since the fluidity of the copolymer consisting mainly of propylene and ethylene was improved, the contrast media such as barium sulfate was evenly distributed (uneven distribution causes fracture). Furthermore, barium sulfate which is uniform micro particle was used as the contrast media, and even when a large quantity of barium sulfate particles was added, the intermolecular bonds of resins were not disturbed, which shows that these particles are effective fillers.

What is claimed is:

1. A root canal filling point which is made of copolymer consisting essentially of propylene and ethylene, and contains a contrast medium.

2. A root canal filling point according to claim 1, wherein the contrast medium is at least one kind of particle selected from the group consisting of barium sulfate, zirconia and titania particles.

3. A root canal filling point according to claim 2, wherein the contrast medium is super-fine particle of barium sulfate having an average particle diameter of 1.0–8.0 $\mu$m.

4. A root canal filling point according to claim 3, wherein the amount of barium sulfate is 40–70% by weight.

5. A root canal filling point according to claim 3, wherein the amount of barium sulfate is 40–70% by weight.

6. A root canal filling point according to claim 1, which is made of an elongated body, and tapered tip having circular cross-section.

* * * * *